United States Patent [19]
Takeda

[11] Patent Number: 4,995,131
[45] Date of Patent: Feb. 26, 1991

[54] ELECTRIC TOOTHBRUSH

[76] Inventor: Hiroshi Takeda, 1-3-15, Tomigaya, Shibuya-ku, Tokyo, Japan

[21] Appl. No.: 438,118

[22] Filed: Nov. 20, 1989

[30] Foreign Application Priority Data

Nov. 25, 1988 [JP] Japan .................................. 63-297822

[51] Int. Cl.$^5$ ............................................. A46B 13/02
[52] U.S. Cl. .................................... 15/22.1; 128/62 A
[58] Field of Search .................. 15/22 R, 22 A, 22 C; 128/62 A

[56] References Cited

U.S. PATENT DOCUMENTS

| 3,978,852 | 9/1976 | Annoni | 15/22 R |
| 4,479,516 | 10/1984 | Hunter | 15/22 R |
| 4,787,847 | 11/1988 | Martin et al. | 15/22 A |

Primary Examiner—Edward L. Roberts
Attorney, Agent, or Firm—Fleit, Jacobson, Cohn, Price, Holman & Stern

[57] ABSTRACT

An electric motor-driven toothbrush comprising a holder having a motor device and a toothbrush member which has a lever releasably adapted to the holder in a cantilever configuration. The toothbrush member has a number of brushing hairs or 'fillings' each of which is thin and resilient, implanted at a brush head portion and a transducer device which converts a rotational movement of a rotor of the motor to a reciprocal linear movement in the direction crossing at right angles to a rotational axis of the rotor. The transducer device is provided at and adjacent to the head portion. The head portion of the brush member is finely and linealy reciprocated at a high speed along the longitudinal direction of each filling.

4 Claims, 2 Drawing Sheets

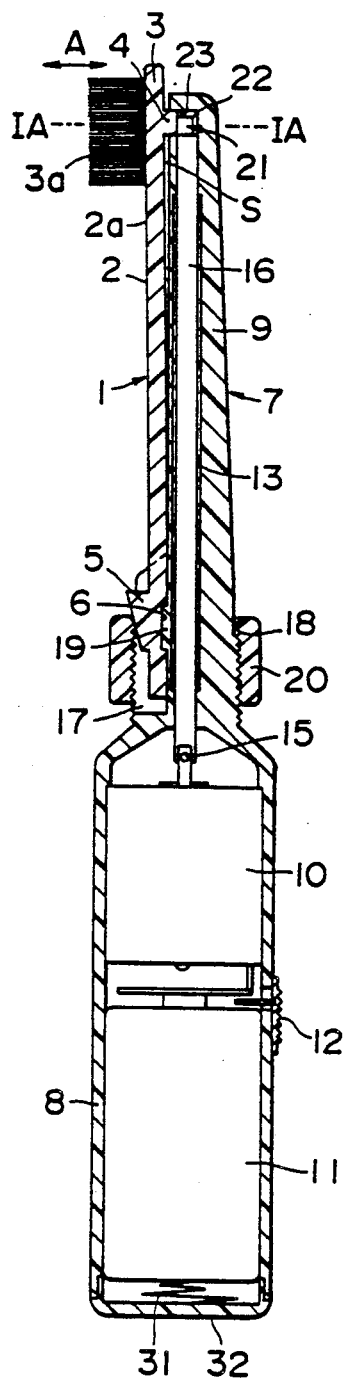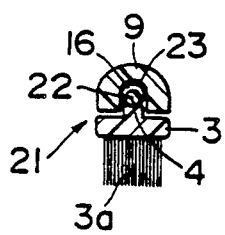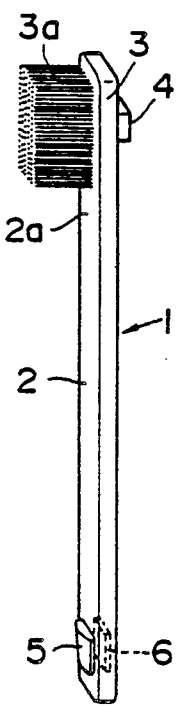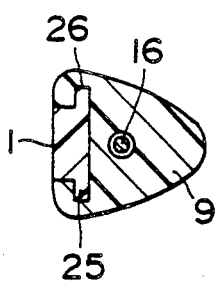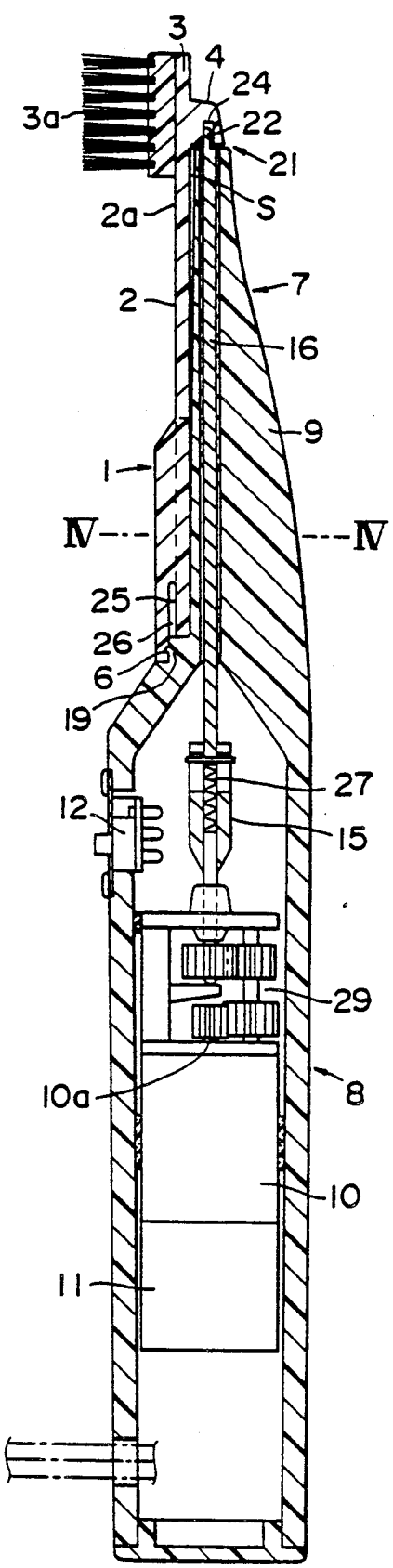

ELECTRIC TOOTHBRUSH

BACKGROUND OF THE INVENTION

The present invention relates to an electric toothbrush and this invention provides a new electric toothbrush which can remove dental, bacterial plaque and keep the oral cavity and teeth clean and healthy to prevent decayed tooth and pyrrhoea, or Rigg's disease, and other diseases of tooth and teethridge or gums.

An electric toothbrush which moves a brush member or fillings i.e., bristles or filaments, back and forth at a high speed in a vertical (up-and-down) or lateral (side-to-side) direction relative to a denture, i.e., an arrangement of teeth, in an arc shape is known and available in the market. In the conventional electric toothbrush, the brush is moved along, and in parallel with, a surface of the tooth, in the same manner as manual toothbrushing.

However, in the conventional manual and automatic toothbrushing operation, in which the brush is moved along, and in parallel with, a surface of the tooth, the brush fillings (i.e., natural or man-made hairs or filaments) are bent and, therefore, only a small force by a bending stress is delivered to a tip of each of the fillings of the brush. Accordingly, it is quite difficult to remove dental, bacterial plaque. Further, since the denture is formed with continuous, irregular undulations of tooth surface, a high speed or high stroke brushing fails to capture the important spots and places such as the portion between adjacent teeth, teethridge, and it is likely that the fillings of the brush jump over these important places to be cleaned where the bacterial plaque adheres. Further, the conventional electric toothbrush has the disadvantage that if it is operated at high speed, it is difficult to handle the toothbrush so that tips of the brush filling are focused on the brushing point. In addition, the conventional electric toothbrush has brush fillings which are stiff and have a stiffness as hard as that of manually operated toothbrushes. Thus, a rapid and-/or large-length movement of the toothbrush causes excoriation of the teethridge and dental abrasion or abrasion of dental tissue.

In general, dental plaque is not so hard, but rather soft, viscous and paste-like. In order to strip off such a dental plaque from the surface of teeth, the applicant has found that it is necessary to push the toothbrush softly in a vertical manner against the tooth surface with the fillings of the toothbrush being erected vertical to the tooth surface so that the fillings can be slightly curved and then moved along the tooth surface by a self-recovery force of the curved fillings of the brush. Thus, the fillings will not jump over the portion to be brushed, but catches the spot of dental plaque. In the present invention, each filling of the brush, which is made, for example, of nylon, is utilized as a 'column' which receives a compression force which induces a bending stress as known in the technological field of material mechanics, and an alternating stress (i.e., alternating compression and tension) is added repeatedly and rapidly to the fillings ('columns') so that stronger force is delivered to tips of the fillings even though each filling has a thickness smaller than the conventional ones. The tips of the brush fillings are rapidly and finely moved to efficiently remove the dental plaque without damage in teethridge.

SUMMARY OF THE INVENTION

An object of the present invention is to provide an improved electric toothbrush.

A further object of the present invention is to provide a new electric toothbrush which can efficiently remove dental plaque without odontic abrasion and excoriation.

According to the present invention, there is provided an electric motor-driven toothbrush comprising a holder having a motor device and a toothbrush member which has a lever releasably adapted to the holder in a cantilever configuration. The toothbrush member has a number of brushing hairs or 'fillings' each of which is thin and resilient, implanted at a brush head portion and a transducer means which converts a rotational movement of a rotor of the motor to a reciprocal linear movement in the direction crossing at right angles to a rotational axis of the rotor. The transducer means is provided at and adjacent to the head portion. The head portion of the brush member is finely and lineally reciprocated at a high speed along the longitudinal direction of each filling.

In a preferred embodiment, the transducer means has an eccentric disc portion at an end of a rotational shaft connected to the rotor shaft of the electric motor, a guide groove formed in a front end of the arm of the holder, and a projection formed integral with the head portion and movable in the guide groove of the holder.

When the electric motor mounted in the holder is driven, the head portion with the fillings is finely moved reciprocally at a high speed in the longitudinal direction of the fillings of the brush. By placing the toothbrush in position so that the filling abut vertically against the surface of the teeth, a larger compression stress is applied to the fillings of the brush in the forward stroke of the reciprocal, linear movement than in the conventional lateral toothbrushing in which the brush fillings are reciprocally moved but in the longitudinal direction of the toothbrush lever so that the fillings of the brush are bent and, accordingly, a resilient force is stored in each of the bent fillings of the brush. The filling ends are then moved along the tooth surface so as to release the stored energy of the resilient force. By this movement of the filling ends, the filling ends "peel off" a part of the dental, bacterial plaque. Thus, a continuous movement of the fillings in a vertical direction relative to a tooth surface can remove the dental plaque effectively, without providing excoriation and abrasion of dental tissue and can establish an effective toothbrushing.

BRIEF DESCRIPTION OF THE DRAWINGS

FIG. 1 is a sectional view of the electric toothbrush embodying the present invention, FIG. 1A is a sectional view taken along line IA—IA in FIG. 1, FIG. 2 is a perspective view of the toothbrush member having a lever and a number of fillings implanted at a surface of a head portion of the lever, FIG. 3 is a sectional view of the toothbrush according to a second embodiment of the present invention, FIG. 4 is a sectional view taken along line IV—IV in FIG. 3.

PREFERRED EMBODIMENTS OF THE INVENTION

Figure 5:
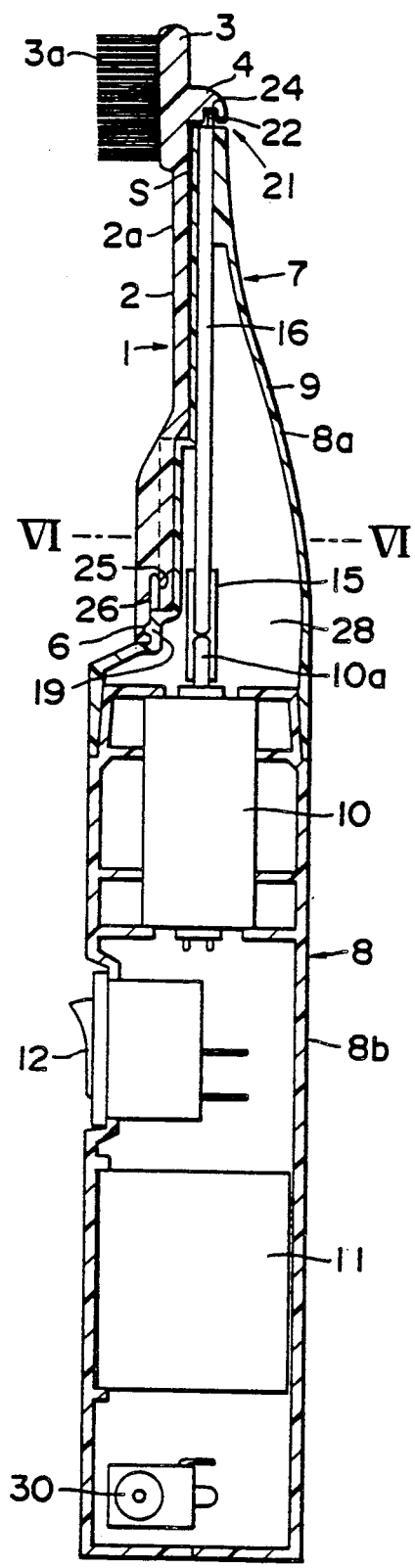
FIG. 5 is a sectional view of the toothbrush according to a third embodiment of the present invention.

With reference to FIGS. 1, 1A and 2 showing a first embodiment of the invention, the electric toothbrush has a toothbrush member 1 and a holder 7 having a tubular casing 8 and a driving system in the tubular casing 8. The toothbrush member 1 is releasably coupled to a predetermined place of the holder 7 in a cantilever arrangement. The toothbrush member 1 has a lever 2 having a head portion 3 at one end, a neck portion 2a adjacent to the head portion 3, and a number of fillings 3a which are made of monofilaments or suitable synthetic resin such as nylon and implanted to a surface of the head portion in a manner similar to that of conventional toothbrushes. In the present invention, the toothbrush member 1 has, at its other end opposite to the head portion 3, a projection 4 on the upper surface of the head portion 3 which surface is opposite to the lower surface where the fillings are implanted and, at the other end, a fixing lug 5 on the lower surface and a recess 6 on the upper surface. In the present invention, the fillings 3a can be thinner and more flexible than the fillings of the conventional toothbrush. The neck portion can be formed thinner to provide a suitable flexibility thereto so as to facilitate a reciprocal movement of the head portion 3 by an electric micro-motor 10 which is known in the art. Reference character "S" represents a small gap between the neck portion 2a of the cantilevered brush member 1 and the arm 9 of the holder 7 for facilitating the reciprocal movement of the head portion 3.

The holder 7 has a tubular body 8 at its rear-half portion and an arm 9 extending from a front end of the tubular body 8. The tubular body 8 has an electric micro-motor 10, a dry cell 11 and an electric switching device 12. The arm 9 has a hole 13 extending along the length of the arm 9 and a rotary shaft 16 extending through the hole 13 and coupled to a rotor shaft 10a of the electric motor 10 through a suitable connector 15. The arm 9 of the holder 7 has, at its base or tail portion, a groove 17 and a projection 19 on the groove surface for engagement with the recess 6 of the brush member 1. A threaded groove 18 is formed on the outer surface of the base portion of the arm 9 so that a fixing nut 20 is threadedly engaged therewith. In order to fit the toothbrush member 1 to the holder 7 in position, the fixing nut 20 is moved toward the tubular body 8 and then the lever 2 of the toothbrush member 1 is inserted into the groove 17 of the arm 9 so that the projection 19 of the arm 9 is fitted to the recess 6 of the toothbrush member 1. Then, the nut 20 is rotated to move toward the head portion 3 to firmly grasp the lug 5 of the toothbrush member 1 to thereby hold the toothbrush member 1 in position in a cantilever configuration.

The arm 9 of the holder 7 has at its tip portion, where the head portion 3 of the toothbrush member 1 is positioned when the toothbrush member 1 is fitted to the holder 7, a transducer 21 which functions to convert a rotational movement of the rotor shaft 10a of the electric motor 10 into a linear, reciprocal movement at right angles relative to the axis of the rotary shaft 16.

The transducer 21 has an eccentric disc 22 which is formed by cutting eccentrically a tip of the rotary shaft 16, a guide hole 23 formed at the arm 9 adjacent to the eccentric disc 22, and the projection 4 of the toothbrush member 1 which is movably held in the guide hole 23. As shown in FIGS. 1 and 1A, the projection 4 of the toothbrush member 1 is contacted directly with the eccentric disc 22 of the rotary shaft 16. The eccentric disc 22 has an eccentricity so that a resultant stroke length of the reciprocal movement is as small as about 1.0 mm. In FIG. 1, reference numeral 32 represents an end cap releasably fitted to an end of the tubular body 8 so that the dry cell 11 is replaceably held in position by the aid of a spring 31.

An operation of the electric toothbrush will be explained. After the toothbrush member 1 is adapted to the holder 7 as illustrated in FIG. 1, the electric motor 10 is driven to rotate the rotary shaft 16 through the connector 15. When the rotary shaft 16 is rotated, the head portion 3 of the toothbrush member 1 is moved reciprocally at a high speed for the small distance determined by the aforementioned transducer 21, as shown by bi-directional arrow (A) in FIG. 1. By the reciprocal, linear movement of the head portion 3, when the toothbrush is positioned in the oral cavity such that the fillings 3a contact the surface of the tooth substantially vertically, the fillings 3a are curved by a compression stress added thereto so that a resilient force is stored in the curved fillings, and the fillings 3a are moved along the tooth surface by a recovery force of the curved fillings 3a. Namely, the recovery force of the curved fillings forces each filling 3a to move along the tooth surface to peel off the dental plaque. This movement of the fillings is repeated at a high speed and accordingly an alternating impact load is produced to effectively brush the teeth.

Referring to FIG. 3 showing a second embodiment of the invention, the projection 4 of the head portion 3 of the toothbrush member 1 has an aperture 24 for receiving the eccentric disc 22 of the rotary shaft 16 and the eccentric disc 22 is contacted directly to an inner top surface 4a so that a rotational movement of the eccentric disc 22 induces a reciprocal movement of the head portion 3 with the fillings 3a. In addition, as shown in FIG. 4, the lever 2 of the toothbrush member 1 has extended portions or wings 25 at its end portion, and the arm 9 has a guide groove 26 for receiving the lever 2 with the wings 25. In the embodiment of FIG. 3, a rotor shaft 10a of the electric motor 10 is coupled to the rotary shaft 16 through a gear device 29 and a connector 15 which has a spiral spring 27 which urges resiliently the rotary shaft 16 in the forward direction. After the tail portion of the lever 2 of the toothbrush member 1 is primarily fitted to the holder 7 as illustrated in FIG. 4, the toothbrush member 1 is pushed rearwardly toward the tubular body 8 so that the projection 4 pushes the tip end of the eccentric disc 22 against a resilient force of the spring 27, and thus the rotary shaft 16 is retracted so that an engagement is made between the recess 6 of the toothbrush member 1 and the projection 19 of the holder 7. Thus, the eccentric disc 22 is received in the aperture 24. In this state, the rotary shaft 16 is projected forwardly by the resilient force of the spring 27, and the toothbrush member 1 is fitted snugly to the holder 7. Thus, the toothbrush member 1 is held in position. If the toothbrush member 1 is to be released from the holder 7 for some reason such as replacing it with a new one, it is sufficient to pull the toothbrush member forwardly to release the engagement between the recess 6 of the lever 2 and the projection 19 of the arm 9 of the holder 7. The toothbrush member 1 can be fitted to the holder 7 much more easily in the embodiment of FIG. 3 than in the embodiment of FIG. 1 which uses the nut 20.

Figure 6:
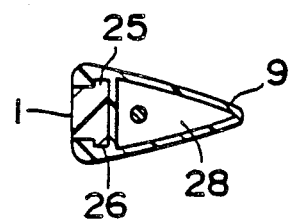
FIG. 6 is a sectional view taken along line VI—VI in FIG. 5.

In the embodiment of FIGS. 1 through 4, the eccentric disc 22 is rotated in one direction. This mode of operation can be modified to a rocking motion by using a suitable rocking mechanism (not shown). FIGS. 5 and 6 show a third embodiment of the invention. In this embodiment, the tubular body 8 consists of two parts, that is, a front portion 8a and a rear portion 8b, which are connected together releasably by a snap-fit connection or the like, or otherwise unreleasably by a suitable adhesive agent. The arm 9 of the holder 7 is a hollow body as illustrated having a space 28 to seek reduction of weight without sacrifice of a suitable mechanical strength and rigidity so that the arm 9 does not deflect along with the reciprocal movement of the head portion 3 of the toothbrush 1. In the embodiment of FIG. 5, the ON-OFF switch 12 in the embodiment of FIG. 3 is positioned at a middle portion of the tubular body 8 whereas the switch 12 is positioned at a front end portion of the tubular body 8. Further, the connector 15 in this embodiment has no spiral spring as the spring 27 of FIG. 3, which, however, can be used if desired also in this embodiment. In FIG. 5, reference numeral 30 represents a connector for charging a rechargeable battery such as a Ni-Cd battery. Other structural and operational features are substantially similar to those of the previous embodiments and will be understood from the description of the previous embodiments.

According to the present invention, a rotational movement of the rotary shaft 16 is converted to a reciprocal movement of the head portion 3 having fillings 3a by the transducer 21, which is positioned above the head portion 3 of the toothbrush member 1 so that the rotational movement of the rotary shaft 16 is converted and directly transmitted to the head portion 3. Accordingly, the reciprocal movement having a very small stroke length of about 1.0 mm by the eccentric disc 22 can be fully transmitted to the fillings 3a. In this respect, if a vibration is added to the base, or tail portion, of the lever 2 of the toothbrush member 1 rather than to the head portion 3, the vibration will be absorbed in the length of the lever 2 and it will not be fully transmitted to the head portion 3 having the fillings 3a and, accordingly, a desired reciprocal movement of the head portion 3 will not be obtained. Further, the toothbrush member 1 is held by the motor device 7 in a cantilever configuration and accordingly, the toothbrush can be located accurately and easily at a predetermined position of the teeth while the head portion 3 is moved reciprocally, without rolling, pitching and other undesirable movement. Thus, a very delicate controlling of the toothbrush for positioning the fillings on the predetermined spot of the teeth can be realized easily. Further, it might be possible to produce a reciprocal movement to the head portion 3 without providing the lever 2 in the toothbrush member 1, but the applicant has found that some disadvantages such as rolling and pitching are produced during toothbrush operation if the tooth brush member 1 does not have a lever as the lever 2. In the present invention, the reciprocal movement of the head portion 3 permits the fillings to reach a thin and narrow spot and catch the dental plaque reliably without excoriation and abrasive damage in dental tissue.

What is claimed is:

1. An electric toothbrush comprising:
   a holder having a tubular body, an electrical driving device in said tubular body, an arm having a longitudinal hole and extending from said tubular body, and a rotary shaft connected to said electrical driving device and extending through said longitudinal hole,
   a toothbrush member having a longitudinal lever, a head portion at an end of said lever, a tail portion at the other end thereof, and brush-fillings implanted in a portion of said head portion,
   transducer means for converting a rotational movement of said rotary shaft to a reciprocal, linear movement to said head portion so that said head portion is reciprocally moved at right angles relative to a longitudinal direction of said rotary shaft, and
   fixing means for releasably holding said tail portion of said lever of the toothbrush member to said arm of said holder in a cantilever configuration.

2. The electric toothbrush according to claim 1, wherein said transducer means comprises an eccentric disc at an end of said rotary shaft, a hole formed at an end portion of said arm adjacent to said eccentric disc, and a projection on said head portion of said toothbrush member so that said eccentric disc contacts said projection to thereby move said head portion linearly and reciprocally.

3. The electric toothbrush according to claim 1, wherein said transducer means comprises an eccentric disc at an end of said rotary shaft, a projection on said head portion of said toothbrush member, and a hole in said projection for rotatably receiving therein said eccentric disc.

4. The electric toothbrush according to claim 3, wherein said toothbrush member has extended portions extending in the opposite directions at said tail portion of said lever, and said arm of said holder has a groove for slidably receiving said extended portions so that said toothbrush member is held by said holder in a cantilever configuration.

* * * * *